United States Patent [19]

Alt

[11] 4,226,615
[45] Oct. 7, 1980

[54] PLANT GROWTH REGULATORS

[75] Inventor: Gerard H. Alt, Creve Coeur, Mo.

[73] Assignee: Monsanto Company, St. Louis, Mo.

[21] Appl. No.: 939,308

[22] Filed: Sep. 5, 1978

Related U.S. Application Data

[63] Continuation-in-part of Ser. No. 537,224, Dec. 30, 1974, abandoned.

[51] Int. Cl.$^2$ ............................................. A01N 9/20
[52] U.S. Cl. ................................ 71/121; 260/566 R; 260/566 F
[58] Field of Search ........... 71/121; 260/566 R, 566 F

[56] References Cited

U.S. PATENT DOCUMENTS

| | | | |
|---|---|---|---|
| 3,478,097 | 11/1969 | Hart et al. | 260/566 R |
| 3,652,770 | 3/1972 | Rohr et al. | 71/121 X |
| 3,721,741 | 3/1973 | Rohr et al. | 71/121 X |
| 3,862,833 | 1/1975 | Johnson et al. | 71/121 |

OTHER PUBLICATIONS

Reisner et al., Chem. Abst., vol. 50 (1956) 854e.
Smith, Chem. Abst., vol. 56 (1962) 10012.

*Primary Examiner*—Catherine L. Mills
*Attorney, Agent, or Firm*—William I. Andress; Donald W. Peterson

[57] ABSTRACT

The disclosure herein pertains to the field of plant growth regulation, particularly the enhancement of pod set and yield in soybeans. The plant growth regulator compositions of this invention contain as the active ingredient salicylideneimines having monohalo-substitution on the benzyl moiety and at least one trifluoromethyl radical and optionally one or more halogen atoms substituted on the anilino moiety.

22 Claims, No Drawings

PLANT GROWTH REGULATORS

CROSS-REFERENCE TO RELATED APPLICATION

This application is a continuation-in-part of U.S. Application Ser. No. 537,224 filed Dec. 30, 1974, now abandoned which is incorporated by reference herein.

BACKGROUND OF THE INVENTION

1. Field of the Invention

The invention herein pertains to the field of substituted salicylideneimines, plant growth regulator compositions containing same and method of use, particularly to enhance pod set and increase yield in soybeans.

2. Description of the Prior Art

The novel compounds described and claimed herein belong to a generic class of compounds variously described as salicylideneimines, salicylidene anilines or formimidophenols. These compounds are Schiff bases prepared, typically, by the reaction of appropriately substituted aromatic amines and salicylaldehydes.

The most relevant prior art known to the inventor herein are U.S. Pat. Nos. 3,652,770 and 3,721,741, both to Rohr et al. The latter patent is a divisional application of the former, hence the disclosures of these patents are identical. Rohr et al disclose, in relevant part, certain salicylideneimines characterized by having a minimum of two halogen atoms fixed in the ortho and para (4 and 6) positions relative to the hydroxyl radical and, optionally, a third halogen in the meta (3) position on the benzyl moiety of the molecule bonded to an anilino moiety which may be substituted with at least one member selected from the group consisting of a halogen atom, $CF_3$, $NO_2$, CN, alkyl, alkoxy, SCN and a tertiary amino group. These compounds are used as active ingredients in phytopathogenic compositions for combatting harmful insects, acarides, nematodes, fungi and bacteria.

The disclosure of Rohr et al exemplifies, e.g., salicylideneimines which have either halogen or $CF_3$ groups on the anilino moiety, but not both simultaneously and this together with the requisite limitation of a minimum of two halogen groups on the benzyl moiety is distinguished from the compounds herein which have but one halogen on the benzyl moiety and, in preferred embodiments, have both halogen and $CF_3$ groups attached to the anilino moiety. The significance of these distinctions will be shown below in comparative tests of the Rohr et al compounds with those disclosed and claimed herein as plant growth regulator compounds—a utility not contemplated by Rohr et al. In most pertinent part, the U.S. Pat. No. 3,652,770 teaches the use of the pertinent compounds in quantities less than herbicidal for the express purpose of combatting phytopathogenic fungi and bacteria, insects, acarides, nematodes. The patentees in the U.S. Pat. No. 3,652,770 recognized that too great a quantity of the relevant compounds would kill plants and inhibit plant growth, but otherwise they failed to observe, appreciate, recognize and/or record any plant growth regulator effect of using the compounds for phytopathogenic animal life.

Other prior art less relevant than the above-mentioned Rohr et al patents include salicylideneimines which have monohalo substitution on the benzyl moiety and one or more halogens substituted on the anilino moiety, but no $CF_3$ substitution as required herein. Exemplary of such art are: U.S. Pat. No. 3,478,097; Chemical Abstract (C.A.) 27, 1335 (1933); C.A. 50 854f (1956); C.A. 55, 5500–5501 (1961) and C.A. 56, 10012 (1962). None of these references disclose any plant growth regulator utility in general or soybean pod set enhancement and yield in particular. Use of a number of the compounds in said C.A. references in the regulation of plant growth is claimed in the inventor's said U.S. Patent Application Ser. No. 537,224.

Yet other less relevant prior art include the polyhalogenated benzylidene benzylamines or benzylidene phenylethylamines of U.S. Pat. No. 3,856,504 and the polyhalogenated benzylideneaniline derivatives disclosed in U.S. Pat. No. 3,862,833. Neither of these patents disclose salicylideneimines which have $CF_3$ radical substitution on the anilino moiety. The relevance of these patents lies in the use of the disclosed compounds as plant growth regulators.

Finally, reference is made to U.S. Pat. No. 3,012,068, relevant only to the extent that the compounds therein are Schiff bases which are toxic to certain parasites and aquatic pests, e.g., insects, fungi, helminths, mites, bacteria, aphids, nematodes, snails and trash fish. Certain of the compounds in the '068 patent have utility for the control of weeds and inhibition of nitrification. The compounds of the '068 patent are characterized by the presence of a methylcarboxoyloxy radical and optionally other substituents and are thus-distinguished from the compounds of this invention.

SUMMARY OF THE INVENTION

This invention relates to a novel class of substituted salicylideneimine compounds, plant growth regulator compositions containing same as active ingredient therein and method of use to control the natural growth or development of dictyledonous plants such as legumes. A more preferred aspect of this invention is the enhancement of pod set and yield increase in soybeans.

The compounds of this invention have the general formula

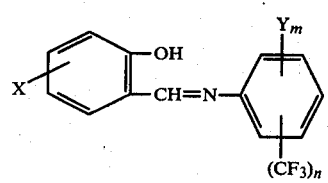

wherein
X and Y independently represent chlorine, bromine or iodine;
m is 0–3 inclusive and
n is 1–3 inclusive.

The preferred species of compounds within the above formula are those wherein X and Y are chlorine, X positioned in the 4 position and Y in the 2 position, m and n are 1 and $-CF_3$ is in the 5 position. The most preferred species is 4-chloro-[N-(2-chloro-5-trifluoromethylphenyl)formimidoyl]phenol.

DETAILED DESCRIPTION OF THE INVENTION

In accordance with this invention a method is provided whereby viable plants are treated with a novel chemical substance which alters their natural growth or development to enhance the various agricultural or horticultural features of the plants. As employed herein, the term "natural growth or development" designates the normal life cycle of the plant in accordance with its genetics and its environment, in the absence of artificial, external influences.

The compositions and method of regulating plant growth provided by this invention are particularly useful for treating dicotyledonous plants to modify the vegetative growth, the flowering or fruit set or to optimize the yield. Representative dicotyledonous crop plants which may be treated with the compounds of this invention include cotton, tomato, coffee and the legumes, for example, soybean, beans, peas and the like, which often do not obtain their yield capacity due to premature blossom drop or because of failure of the fruit to set.

Of particular use and interest herein certain of the compounds of this invention are useful in enhancing pod set and increasing the yield of soybeans.

For convenience, the term "active ingredient" will be used hereinafter to denote one or more of the salicylideneimines as previously defined.

It is to be understood that the regulation of natural growth and development does not include killing or herbicidal action. Although phytotoxic or lethal amounts of the active ingredient might be employed to destroy certain plants, it is contemplated here to employ only such non-lethal amounts of said active ingredient as will serve to regulate the natural growth and development of useful plants without substantial injury. As may be expected and as long understood by those skilled in the art, such effective plant regulating amounts will vary, not only with the particular active ingredient selected for treatment, but also with the regulatory effect to be achieved, the species of plant being treated and its stage of development, and whether a permanent or transient regulating effect is sought. Other factors which may bear upon the determination of an appropriate plant regulating amount include the plant growth medium, the manner in which the treatment is to be applied, weather conditions such as temperature or rainfall, and the like.

In accordance with the instant invention it has been found that desirable regulation of natural plant growth or development is achieved by application of the active ingredient to plants in various stages of development. Accordingly, in the practice of this invention the active ingredient can be applied to the soil habitat of the plant or directly to the plant in the seedling stage, flowering stage or fruiting stage and the like or can be applied sequentially to plants at more than one stage of development. Such application may be made directly to one or more of the plant's parts, such as stems, leaves, flowers, fruit or the like. Generally, the application is made by spraying the plants using conventional techniques.

Regulation of the natural growth or development of plants by chemical treatment results from the effect of the chemical substance on the physiological processes of the plant and the effect of such substance may be manifested by the morphology of the plant. As should be readily apparent, said regulation may also result from a combined or sequential effect of the chemical manifesting a response in both physiology and morphology.

In general, regulation of the natural growhh or development which leads to a morphological change in the plant is readily noticeable by visual observation. Such changes can be found in the size, shape, color or texture of the treated plant or any of its parts. Included among possible regulatory effects are the inducing of axillary bud development, alteration of shape of leaf or canopy, delay or acceleration of fruit or pod set, dry weight accumulation, stature reduction, branching, terminal inhibition, reduced transpiration or increased carbohydrate deposition or protein content, etc. Similarly, changes in the quantity of plant fruit or flowers can be simply noted.

On the other hand, regulation which leads to changes only in the physiological processes occur within the treated plant and are usually hidden from the eye of an observer. Changes of this type are most often in the production, location, storage or use of naturally occurring chemicals, including hormones, within the plant. Physiological changes in a plant often are recognized when followed by a subsequent change in morphology. Additionally, there are numerous analytical procedures known to those skilled in the art for determining the nature and magnitude of changes in the various physiological processes.

The individual compounds of the instant invention serve to regulate the natural growth or development of treated plants in a number of diverse ways, and it is to be understood that each compound may not produce identical regulatory effects on each plant species or at every rate of application. As stated above, responses will vary in accordance with the compound, the rate, the plant, etc. Thus, one response may occur in conjunction with other responses, but may occur separately. For example, depending upon various factors realized by those skilled in the art to effect activity, the data illustrated below demonstrates that the compounds of the present invention sometimes alter the leaf morphology even though the plants are not reduced in stature.

Alteration of the leaf morphology of leguminous plants is important because leguminous plants have canopies that effectively inhibit sunlight from reaching the lower leaves. For example, only about 50% of a soybean plant's leaves intercept light for photosynthesis. Approximately 85% of the light is absorbed by the outer layer of leaves. Many researchers feel that by altering the morphology of the leaves such that the canopy is altered, light may fall more deeply into the canopy, and yields could be increased. Weber, in "Field Crop Abstracts", Volume 21, No. 4, pages 313–317, states that "greater light penetration, resulting in greater amount of the [soybean] plant canopy having a light intensity above 150, f.c., generally led to higher seed yields." Johnson et al, in "Crop Science", Volume 9, pages 577–581, states that "adding light increased the yields of bottom, middle and top canopy positions of [soybean] plants 30, 20 and 2%, respectively." Thus, it would be highly beneficial if a method was found whereby the leaves of such plants could be altered such that a greater number of leaves could be illuminated.

Another regulatory response demonstrated by many compounds useful in the practice of this invention can be generally termed retardation of vegetative growth and such a response has a wide variety of beneficial features. In certain plants this retardation of vegetative growth causes a diminution or elimination of apical dominance leading to a shorter main stem and increased lateral branching. This regulation of the natural growth or development of plants produces smaller, bushier plants which often demonstrate increased resistance to climatic extremes, pest infestations and the like. Thus, compositions used in the method of this invention provides for plants that are in a good state of health and tends to produce more vigorous plants.

As illustrated in the treatments hereinafter presented, the individual compounds of this invention regulate the natural growth or development of treated plants in one or more of the above respects.

Although regulatory effects such as those described above can be desirable, often it is the ultimate result of these effects upon the economic factor which is of primary significance in crop plants or upon the aesthetic factor in ornamental plants. Thus, it must be recognized that increases in yield of individual plants, increases in the yield per unit of cropping area, improvement in the quality of the plants' product, improvement in the plants' vigor and reductions in the cost of harvesting and/or subsequent processing are all to be considered in any assessment of the consequence of an individual regulatory effect during the growth or development of a plant.

The practice of this invention is particularly useful for improving the efficiency of dicotyledonous row crops such as soybean, tomatoes and cotton. The application of the compounds of this invention to such growing crop plants often reduces the stature of the plants without the expected substantial reduction in seed yield. In this manner the plant's efficiency of production is improved and a means is provided for optimizing the crop by increasing the plant population per unit area and treating said crop with the active ingredient during its growing stage. Such reduction in plant stature also increases accessibility to the field for other treatments, cultivation and harvesting.

One aspect of this invention is the provision of a plant growth regulating composition comprising an effective plant growth regulating amount of the salicylideneimine compounds described above and an adjuvant. The plant growth regulating compositions are particularly effective for practicing the method of regulating the natural growth or development of plants provided by this invention. In view of the activity of the active ingredients at low rates of application, it is desirable to use compositions comprising an effective amount of the active ingredient and an adjuvant to facilitate a uniform distribution of the compound on the plants. Adjuvant, as used herein, includes one or more materials in liquid or solid form. Thus, suitable adjuvants are diluents, extenders, carriers, surfactants, foaming agents, conditioning agents, solvents and, usually, combinations thereof. The compositions can be in numerous forms, such as, dusts, powders, water soluble powders, wettable powders, solutions, foams, dispersions or emulsions. Generally, it is preferred to use one or more surfactants in the plant growth-regulating compositions which aid in wetting the treated plant surface and for providing stable dispersions of the active ingredient in various inert carriers or diluents in the composition or added to the composition prior to application to the plants. Suitable surfactants which can be employed in the compositions of this invention are well known surface active agents, such as, wetting agents, emulsifiers, dispersing agents and can be nonionic, anionic or cationic. Preferred surfactants are the nonionic or the anionic type which are widely used in compositions employed in agronomic treatments. Representative nonionic surfactants are polyoxyethylene esters of fatty acids, octylphenyl polyethylene glycol ethers, polyoxyethylene derivatives of long-chain alcohols and the like. Representative anionic surfactants are alkali and alkaline earth salts of alkylarylsulfonic acids such as sodium lauryl sulfonate, dialkyl sodium sulfosuccinate esters and the like. Such surfactants are well known and reference is made to U.S. Pat. No. 2,547,724 for detailed examples of same.

Usually the plant growth-regulating compositions of this invention take the form of a concentrate which can be readily extended with an inert carrier prior to application to the plants. Said concentrates in liquid form generally consist of a solvent, surfactant, emulsifier, defoamer and/or other additive and about 1–95% by weight of the active ingredient. These liquid concentrates can be diluted with water to provide a composition, suitable for application to plants, which contains from about 0.1 to about 15%, and commonly from about 1.0 to 10% by weight of the active ingredient. Concentrates in solid form are, for example, water soluble powders consisting of finely divided solids such as calcium silicate, surfactant and from about 1–95% or more by weight of the active ingredient which are diluted with water prior to applying to the plants.

Broadly, the plant growth regulator compositions herein may contain from 0.1 to 95% (more or less) by weight of the active ingredient. These compositions may be applied at rates of from 0.05 to 20 lb/acre (0.168 to 22.4 kg/ha) or more, a preferred range being from 1.0–10 lb/ac. (1.12 to 11.2 kg/ha) as more particularly detailed below.

In selecting the appropriate non-lethal rate of application of the active ingredient, it will be recognized that precise dosages will be dependent upon the plant species being treated, the particular plant part or habitat to which application is made, the development stage of the plant, the particular chemical employed, the mode of application and various other factors known to those skilled in the art. In foliar treatment for the regulation of plant growth, the active ingredients are applied in amounts from about 0.05 to about 10 or more pounds per acre (0.168 to 11.2 kg/ha). Foliar applications of from 0.1 to 6 pounds of the active ingredient per acre (0.112 to 6.72 kg/ha) are preferred. In applications to the soil habitat of the plants the active ingredients are applied in amounts of from about 0.01 to about 20 pounds per acre (0.011 to 22.4 kg/ha) or more. Preferably, the active ingredients are applied to the soil at a rate of from 0.1 to 10 pounds per acre (0.11 to 11.2 kg/ha) and in particular embodiments at rates of from 1 to 6 lb/ac. (1.12 to 6.72 kg/ha). Foliar application to plants at the blooming stage, e.g., 10% blossoms, are particularly advantageous and are preferred.

The salicylideneimines of this invention are prepared by known methods as outlined in the foregoing description of the prior art.

In specific working embodiments, the preparation of exemplary compounds of this invention will be described in the examples below. The same procedure in Example 1 was followed in order to prepare the compounds of Examples 2–10, but substituting the appropriate aromatic amine and aromatic aldehyde. In all examples below the elemental analyses values are in percentages.

EXAMPLE 1

To 0.02 mol of 2-chloro-5-trifluoromethylaniline in 25 ml of hot ethanol was added 0.02 mol of 5-chloro-o-salicylaldehyde in 25 ml of hot ethanol. The reaction mixture was heated to reflux for 15 minutes and the product crystallized on cooling. Recrystallization from ethanol or a chloroform/ethanol mixture gave analytically pure material of yellow needles. The product had a melting point of 120°–122° C., mol. wt. 334.14, and was identified as 4-chloro-2-[N-(2-chloro-5-trifluoromethylphenyl)formimidoyl]-phenol.

Anal. Calc'd for $C_{14}H_8O_2F_3NO$: C, 50,32; H, 2.41. Found: C, 50.44; H, 2.47.

EXAMPLES 2–10

Following substantially the same procedure described in Example 1, the compounds listed in Table 1 were prepared and had the physical properties and elemental composition shown for the respective compounds. Minor variations in procedure involve refluxing up to 30 minutes and/or concentrating prior to cooling and recrystallization.

TABLE I

| Example No. | Compound | Empirical Formula | M.P. (mm Hg) | Element | Analysis Calculated | Found |
|---|---|---|---|---|---|---|
| 2 | 4-Bromo-2-[N-(2-chloro-5-trifluoromethylphenyl)formimidoyl]phenol | $C_{14}H_8BrClF_3NO$ | 119–121 | C | 44.41 | 44.59 |
|   |   |   |   | H | 2.13 | 1.92 |
| 3 | 4-Chloro-2-[N-(3,5-ditrifluoromethylphenyl)formimidoyl]phenol | $C_{15}H_8ClF_6NO$ | 119–121 | C | 49.00 | 49.32 |
|   |   |   |   | H | 2.19 | 2.36 |
| 4 | 4-Bromo-2-[N-(3-trifluoromethylphenyl)formimidoyl]phenol | $C_{14}H_9BrF_3NO$ | 104–106 | C | 48.86 | 48.90 |
|   |   |   |   | H | 2.64 | 2.66 |
|   |   |   |   | N | 4.07 | 4.11 |
| 5 | 4-Bromo-2-[N-(3,5-ditrifluoromethylphenyl)formimidoyl]phenol | $C_{15}H_8BrF_6NO$ | 136–138 | C | 43.71 | 43.61 |
|   |   |   |   | H | 1.96 | 1.88 |
|   |   |   |   | N | 3.40 | 3.65 |
| 6 | 4-Chloro-2-[N-(3-trifluoromethylphenyl)formimidoyl]phenol | $C_{14}H_9ClF_3NO$ | 82–84 | C | 56.11 | 55.47 |
|   |   |   |   | H | 3.03 | 3.01 |
|   |   |   |   | N | 4.67 | 4.76 |
| 7 | 4-Chloro-2-[N-(4-trifluoromethylphenyl)formimidoyl]phenol | $C_{14}H_9ClF_3NO$ | 100–102 | C | 56.11 | 56.60 |
|   |   |   |   | H | 3.03 | 3.10 |
|   |   |   |   | N | 4.67 | 4.75 |
| 8 | 4-Chloro-2-[N-(2-trifluoromethylphenyl)formimidoyl]phenol | $C_{14}H_9ClF_3NO$ | 50–53 | C | 56.11 | 56.36 |
|   |   |   |   | H | 3.03 | 3.09 |
|   |   |   |   | N | 4.67 | 4.67 |
| 9 | 4-Chloro-2-[N-(3-trifluoromethyl-4-Bromo-phenyl)formimidoyl]phenol | $C_{14}H_8BrClF_3NO$ | 110–112 | C | 44.42 | 44.38 |
|   |   |   |   | H | 2.13 | 2.14 |
|   |   |   |   | N | 3.70 | 3.73 |
| 10 | 4-Chloro-2-[N-(2-trifluoromethyl-4-Chlorophenyl)formimidoyl]phenol | $C_{14}H_8Cl_2F_3NO$ | 126–128 | C | 50.33 | 50.37 |
|   |   |   |   | H | 2.41 | 2.46 |
|   |   |   |   | N | 4.19 | 4.18 |

Other species of compounds within the purview of and corresponding to the general formula of this invention are listed in Examples 11–35; these compounds are similarly prepared as those in the preceding examples.

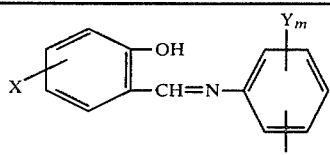

| Ex. No. | X Position | Y Position | m | CF$_3$ Position | n |
|---|---|---|---|---|---|
| 11 | 3-Cl | 2,6-diCl | 2 | 4 | 1 |
| 12 | 3-Cl | 3,5-diCl | 2 | 4 | 1 |
| 13 | 3-Cl | 2,3,5-triCl | 3 | 4 | 1 |
| 14 | 3-Cl | 2,3,4-triCl | 3 | 6 | 1 |
| 15 | 3-Br | 2,6-diBr | 2 | 4 | 1 |
| 16 | 3-Br | 3,5-diBr | 2 | 4 | 1 |
| 17 | 3-Br | 2,3,5-triBr | 3 | 6 | 1 |
| 18 | 3-Br | 2,6-diBr | 2 | 4 | 1 |
| 19 | 3-Br | 3,5-di | 2 | 4 | 1 |
| 20 | 5-Cl | 2-Cl | 1 | 5 | 1 |
| 21 | 5-Br | 2-Cl | 1 | 5 | 1 |
| 22 | 5-Cl | — | 0 | 3,5 | 2 |
| 23 | 5-Br | — | 0 | 3 | 1 |

-continued

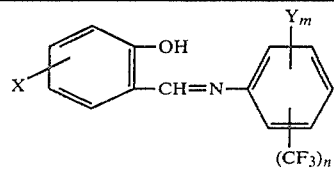

| Ex. No. | X Position | Y Position | m | CF$_3$ Position | n |
|---|---|---|---|---|---|
| 24 | 5-Br | — | 0 | 3,5 | 2 |
| 25 | 5-Cl | — | 0 | 3 | 1 |
| 26 | 5-Cl | — | 0 | 4 | 1 |
| 27 | 5-Cl | — | 0 | 2 | 1 |
| 28 | 5-Cl | Br | 1 | 3 | 1 |
| 29 | 5-Cl | Cl | 1 | 2 | 1 |
| 30 | 4-Cl | — | 0 | 3,4,5 | 3 |
| 31 | 4-Cl | — | 0 | 2,4,6 | 3 |
| 32 | 4-I | 2-Cl | 1 | 5 | 1 |
| 33 | 4-I | 4-Br | 1 | 3 | 1 |
| 34 | 4-I | 4-Cl | 1 | 2 | 1 |
| 35 | 4-I | 4-I | 1 | 3 | 1 |

The particular beneficial utility of the preferred compound of this invention, i.e., the compound of Example 1, is shown by reference to field test data demonstrating soybean yield increase expressed in several components relative to control plants, e.g., bushels per acre, seeds per square foot, hundred seed weight, seed size and seed number. Field tests were conducted at St. Charles, Missouri and in Santiago Chile. Example 36 describes the St. Charles tests and data and Example 37 describes the Santiago tests and data.

EXAMPLE 36

In this example the effect of 4-chloro-2-[N-(2-chloro-5-trifluoromethylphenyl)formimidoyl]phenol on soybean yield enhancement components resulting from field tests in St. Charles, Missouri is shown in Table 2 below.

Plots of soybean plants (Williams variety) growing in 11-inch (27.94 cm) row spacings 5 seeds/row ft (30.5 cm) and having an intended population density at harvest of 255,000 plants/acre (630,000 plants/ha) were treated with an emulsifiable concentrate containing 1.5 lb/gal (0.18 kg/L) of the above compound as active ingredient in a $C_9$ aromatic solvent (T400) at rates of 0.5, 1.0 and 2.0 lb/A (0.56, 1.12 and 2.24 kg/ha), respectively, of active ingredient. The application volume was 30 gpa. A surfactant comprising a 0.05% v/v mixture of Flo-Mo and Etlox 3437-F was used as surfactant in the treatments. Other surfactants such as Tween 20 (polyoxyethylene (20) sorbitan monolaureate) may also be used.

The above plant growth regulator solution was applied at two different stages, vis., when 50% of the soybean population was flowering (F) and at early pod fill (EP). By definition the flowering stage is when 50% of the plant population has at least one flower and early pod fill is when at least one pod at any of the fourth to seventh nodes above the ground begins to fill on 50% of the plant population. At harvest, the treated plants were compared to the untreated control plants growing under identical conditions of row spacing and population density. The results of these tests representing an average of four replications are shown in Table 2.

In the table, the data in parenthesis in the last four columns expresses the actual quanta for the untreated control plants; the numerical values for the treated plants represent percentages of control plant data.

at the flowering stage. At harvest, the treated plants were compared to untreated control plants growing under same conditions of row spacing and population density. The results of these tests (average of four replications) are shown in Table 3.

In Table 3, the data in parenthesis in the last four columns again represent actual values for the control plants, while the numerical figures for the treated plants represent the percentage change from the values for the control plants. The first crop of soybean seeds were planted on day D, the second crop 18 days later D+18 and the third crop 28 days latter on D+28.

TABLE 3

| Planting Date (D) | Rate Lb/A | (Kg/Ha) | Yield Bu/A | (Kg/Ha) | Seed Size Mg/- Seed | Seed Number (Seeds/- 10 cm$^1$) |
|---|---|---|---|---|---|---|
| D | 0 | | (47) | (3161) | (153) | (42) |
| D | 0.5 | (0.56) | +16 | | +7 | +8 |
| D | 1.0 | (1.12) | +8 | | -1 | +9 |
| D | 2.0 | (2.24) | +4 | | +5 | -2 |
| D + 18 | 0 | | (37) | (2488) | (131) | (38) |
| D + 18 | C.5 | (0.56) | +3 | | +1 | +1 |
| D + 18 | 1.0 | (1.12) | +7 | | +3 | +4 |
| D + 18 | 2.0 | (2.24) | +17 | | +4 | +13 |
| D + 28 | 0 | | (39) | (2622) | (140) | (38) |
| D + 28 | 0.5 | (0.56) | +12 | | +1 | +11 |
| D + 28 | 1.0 | (1.12) | +25 | | +1 | +23 |
| D + 28 | 2.0 | (2.24) | +15 | | -5 | +21 |

TABLE 2

| Rate Lb/A | (Kg/Ha) | Stage | Yield$^a$ Bu/A | (Kg/Ha) | Population × 10$^3$/A | (10$^3$/Ha) | Seeds/ Ft$^2$ | (M$^2$) | Hundred Seed Weight (Grams) |
|---|---|---|---|---|---|---|---|---|---|
| 0 | | | (57) | (3833) | (255) | (630) | (181) | (1946) | (19.8) |
| 0.50 | (0.56) | F | 111 | | 95 | | 113 | | 97 |
| 1.00 | (1.12) | F | 116 | | 86 | | 119 | | 97 |
| 2.00 | (2.24) | F | 112 | | 118 | | 115 | | 96 |
| 0.50 | (0.56) | EP | 91 | | 96 | | 96 | | 95 |
| 1.00 | (1.12) | EP | 109 | | 116 | | 111 | | 98 |
| 2.00 | (2.24) | EP | 116 | | 113 | | 118 | | 97 |

$^a$Yield of controls at 13% moisture

The data in Table 2 clearly demonstrate enhancement of soybean pod retention as shown by the seeds/unit area and yield at all test rates except for plants treated at the 0.5 lb/A rate at the early pod fill stage of application. Thus, for soybean plants treated at the flowering stage, the increases in yield vis-a-vis in the controls were 11% at 0.50 lb/A (0.56 kg/ha), 16% at 1.00 lb/A (1.12 kg/ha) and 12% at 2.00 lb/A (2.24 kg/ha). For soybean plants treated at the early pod fill stage, the yield relative to controls descreased at the 0.50 lb/A rate, but increased 9% and 16% respectively at the 1.0 and 2.0 lb/A rates. Similarly, the number of soybean seeds per square foot increased for all treated plants, except those treated at 0.50 lb/A rate applied at the early pod fill stage. The decrease in hundred seed weight, of course, indicates a descrease in average soybean seed size.

EXAMPLE 37

This example describes the tests and data resulting from field tests of the plant growth regulator compound of Example 1 in Santiago, Chile.

The same general procedure set forth in Example 36 was followed, except the soybeans (Williams) were thinned to a population density of 150,000 plants/A (345,000 plants/ha) in 20-inch (50.8 cm) row spacings; three (3) different crops of Williams soybeans were planted on three different dates. The plants were treated As is apparent from the data in Table 3, treatment of soybeans with the compound of Example 1 resulted in increases in sobyean yield, seed size and seed number at all rates of application for each of the three crops treated, except for the relatively insignificant decrease of 1% in seed size on plants planted on day D and treated at 1 lb/A and a 5% decrease in seed size on plants planted on day D+28 and treated at 2.0 lb/A, and a 2% decrease in seed number for plants planted on day D and treated at 2.0 lb/A. In most instances, the increases in soybean yield, seed size and seed number are very significant. For example, particular attention is directed to the yield increases and to seed numbers for soybeans treated at all rates of application for soybeans planted on days D and D+28 and at 2.0 lb/A on sobyeans planted on D+18.

The data in Table 3 clearly demonstrate enhanced soybean pod retention and yield resulting from increased seed size as well as seed number.

In addition to the field tests mentioned above, greenhouse tests were conducted in an effort to determine the relative efficacy as plant growth regulators of representative compounds of this invention vis-a-vis the closest known analogs thereof in the prior art. Accordingly, since the abovementioned U.S. Pat. Nos. 3,652,770 and 3,721,741 (a division of the U.S. Pat. No. 3,652,770) are the only prior art references known to the inventor herein disclosing compounds having one or more trifluoromethyl radicals substituted on the anilide moiety of dihalogen-substituted salicylideneimines, comparative tests were made between relevant compounds therein and their monohalogenated salicylideneimine analogs disclosed herein. In addition, comparative tests were conducted between compounds which are not specifically exemplified in U.S. Pat. Nos. 3,652,770 and 3,721,741, i.e., those having both a halogen and a trifluoromethyl radical attached to the aniline moiety of the salicylideneimine compound. The results of these tests are shown in Table 4. Mention is made here that the compounds of Examples 2 and 3 were not included in these particular tests, but data generated earlier for these compounds in similar tests was used for comparative purposes here. Accordingly, some variation in data might arise in head-to-head comparative tests. The tested prior art compounds of said U.S. Pat. No. 3,652,770 and 3,721,741 are identified as follows:

A. 4,6-dibromo-2-[N-(3-trifluoromethylphenyl)formimidoyl]phenol.
B. 4,6-dichloro-2-[N-(3-trifluoromethylphenyl)formimidoyl]phenol.
C. 4,6-dibromo-2-[N-(3,5-ditrifluoromethylphenyl)formimidoyl]phenol.
D. 4,6-dichloro-2-[N-(3,5-ditrifluoromethylphenyl)formimidoyl]phenol.
E. 4,6-dibromo-2-[N-(2-chloro-5-trifluoromethylphenyl)formimidoyl]phenol.
F. 4,6-dichloro-2-[N-(2-chloro-5-trifluoromethylphenyl)formimidoyl]phenol.

The comparative tests were conducted as follows: by an "X" under the numerical symbols having the following meanings:

1. Chlorosis
3. Axillary bud development
6. Stem distortion
7. Leaf distortion
8. Leaf alteration
9. Leaf inhibition
11. Rosette growth
12. Altered canopy
13. Thick leaf texture
14. Dark foliar color
26. Inhibition of apical development
39. Stature reduction As will be appreciated by those skilled in the art, not all of the above plant responses are indicative of beneficial plant growth regulator activity. For example, chlorosis (1), stem distortion (6) and leaf distortion (7) alone or in combination are generally not desirable because they are usually indicative of a phytotoxic response. In addition, a severe leaf and/or stem distortion can cause an altered canopy, but in such case the result would not be considered a desirable effect. On the other hand, true plant growth regulator activity, e.g., axillary bud development (3), leaf alteration (8), leaf inhibition (9), altered canopy (12), inhibition of apical development (26), dark foliar color (14), stature reduction (39), and in the case of some plants, e.g., soybeans, early pod set, enhanced pod set, development, retention and yield, will predominate even though some phytotoxic or negative plant responses are also indicated. These phytotoxic effects are generally rate responsive and do not appear at lower rates.

TABLE 4

| Compound | Rate Lb/A | (Kg/Ha) | 1 | 3 | 6 | 7 | 8 | 9 | 11 | 12 | 13 | 14 | 26 | 39 |
| --- | --- | --- | --- | --- | --- | --- | --- | --- | --- | --- | --- | --- | --- | --- |
| A | 3.0 | (3.4) |   |   |   | X |   |   |   | X |   |   |   |   |
| v. |   |   |   |   |   |   |   |   |   |   |   |   |   |   |
| Ex. 4 | 3.0 | (3.4) | X |   |   | X | X | X |   | X |   |   | X | X |
| B | 3.0 | (3.4) | X |   |   | X |   |   |   |   |   |   |   |   |
| v. |   |   |   |   |   |   |   |   |   |   |   |   |   |   |
| Ex. 6 | 3.0 | (3.4) | X | X |   | X | X | X |   | X |   |   |   |   |
| C | 3.0 | (3.4) |   |   | X | X |   |   |   | X |   |   |   |   |
| v. |   |   |   |   |   |   |   |   |   |   |   |   |   |   |
| Ex. 5 | 3.0 | (3.4) |   |   |   | X | X | X |   | X |   |   |   |   |
| D | 3.0 | (3.4) |   |   |   | X |   |   |   | X |   |   |   |   |
| v. |   |   |   |   |   |   |   |   |   |   |   |   |   |   |
| Ex. 3 | 3.0 | (3.4) |   | X |   |   |   | X |   |   |   |   | X |   |
| E | 3.0 | (3.4) |   |   | X | X |   |   |   | X |   |   |   |   |
| v. |   |   |   |   |   |   |   |   |   |   |   |   |   |   |
| Ex. 2 | 3.0 | (3.4) | X |   |   |   |   |   |   |   |   |   | X |   |
| F | 3.0 | (3.4) |   |   |   | X |   |   |   |   |   |   |   |   |
| v. |   |   |   |   |   |   |   |   |   |   |   |   |   |   |
| Ex. 1 | 3.0 | (3.4) |   |   |   | X | X | X |   | X |   |   |   |   |

A standard solution comprising the equivalent concentration of 3 lb/A (3.4 kg/ha) of the test compound in a 50% solution of aqueous acetone solvent containing a 0.25% solution of Tween 20 emulsifier was used. The test solution was applied foliarly to soybean plants (Williams variety) at the 2.5–3.0 leaf (trifoliate stage), i.e., about 3 weeks after planting. Test results were read within 8–10 days after treatment with the test solutions.

In Table 4, the compounds of U.S. Pat. Nos. 3,652,770 and 3,721,741 (4,6-dihalogenated on the salicylyl moiety) are designated by the letters A–F and the corresponding monohalosalicylyl analogs of this invention (the halogen being in the 4 or p-position relative to the hydroxyl radical) are designated by example number. The plant response for each compound is indicated The test data in Table 4 clearly demonstrate that as a class the trifluoromethylphenyl-substituted monohalosalicylideneimine compounds of this invention are biologically more active and indicative of more diverse plant growth regulator applications and effects than are the prior art dihalo analogs thereof as a class. Thus, it will be noted in Table 4 that all of the prior art compounds produced only plant responses that are not considered desirable. Although compounds A and C–E exhibited an altered canopy, this effect was accompanied only by phytotoxic responses, e.g., chlorosis, stem distortion and/or leaf distortion, with no other observed plant growth regulator activity; hence, the effect in such instances is not considered desirable or beneficial. In sharp contrast, while some of the compounds of this invention produced instances of minor phytotoxic effects, such effects were always in conjunction with and subordinated by a plurality of beneficial plant growth regulator responses; in such instances, an altered canopy effect is considered desirable. Particular attention is directed to markedly superior plant growth regulator activity of the compounds of Examples 1, 4, and 6, and to a lesser extent the compounds of Examples 3 and 5 vis-a-vis their dihalogenated counterparts. The comparisons between the compounds of Example 2 and Example 3 and their dihalo analogs show only beneficial plant growth regulator effects for the former compounds, whereas the prior art compounds produce altered canopy associated with phytotoxic effects.

The above data in Table 4 compares the compounds of this invention with the prior art compounds most closely related in structure. However, because the inventor herein has determined that other compounds of the prior art having similar structure also have plant growth regulator activity (to which claim is made in the parent of this application), additional comparisons were made to confirm the relative merits of those compounds vis-a-vis those claimed herein with respect to plant responses in soybeans. These comparisons were made with prior art mono-halosalicylidenimenes having one or two halogen atoms substituted on the anilino moiety as disclosed in the above-mentioned Chemical Abstracts references with compounds of this invention having the same structure but for the substitution of a trifluoromethyl raidcal for a halogen atom on the anilino moiety.

The prior art halosalicyclideneimines in these comparisons are identified as follows:

G. 4-Chloro-2-[N-(3-chlorophenyl)formimidoyl]phenol.
H. 4-Bromo-2-[N-(3-chlorophenyl)formimidoyl]phenol.
I. 4-Chloro-2-[N-(2,5-dichlorophenyl)formimidoyl]phenol.
J. 4-Bromo-2-[N-(2,5-dichlorophenyl)formimidoyl]phenol.
K. 4-Chloro-2-[N-(3,4-dichlorophenyl)formimidoyl]phenol.

Following the general procedure described above, the data in Table 5 was obtained. In Table 5, the prior art compounds are identified as above by the letters G–K and the corresponding trifluoromethyl-substituted analogs of this invention are designated by example number. The plant response for each compound is identified by an "X" under the numerical symbols having the same meanings identified above.

TABLE 5

| Compound | Rate Lb/A | Rate (Kg/Ha) | 1 | 3 | 6 | 7 | 8 | 9 | 11 | 12 | 13 | 14 | 26 | 39 | No. of Tests |
|---|---|---|---|---|---|---|---|---|---|---|---|---|---|---|---|
| G | 3.0 | (3.4) | X |   |   | X |   |   |   |   |   | X |   |   | (1) |
| v. Ex. 6 | 3.0 | (3.4) | X | X |   | X | X | X |   | X |   |   |   |   | (1) |
| H | 3.0 | (3.4) | X |   |   | X | X |   |   |   |   | X |   |   | (2) |
| v. Ex. 4 | 3.0 | (3.4) | X |   |   | X | X | X |   | X |   |   | X | X | (1) |
| I | 6.0 | (6.7) |   | X |   | X | X | X |   |   | X |   | X |   | (3) |
|   | 3.0 | (3.4) |   | X |   |   |   |   |   |   | X |   | X |   | (1) |
| v. Ex. 1 | 6.0 | (6.7) | X | X |   |   | X |   | X | X |   | X |   |   | (3) |
|   | 3.0 | (3.4) |   | X |   |   | X |   |   |   | X | X |   |   | (1) |
| J | 6.0 | (6.7) |   | X | X | X | X |   |   |   | X |   | X |   | (3) |
|   | 3.0 | (3.4) |   |   | X |   | X |   |   |   | X |   |   |   | (1) |
|   | 1.2 | (1.3) | X |   |   |   | X |   |   |   | X |   |   |   | (1) |
| v. Ex. 2 | 6.0 | (6.7) | X |   |   |   |   | X |   |   |   |   |   |   | (1) |
|   | 3.0 | (3.4) | X |   |   |   |   |   |   |   |   |   | X |   | (1) |
|   | 1.2 | (1.3) | X |   |   |   | X |   |   |   |   |   | X |   | (2) |

The data in Table 5 indicates a generally higher rate of plant growth regulator effects for the compounds of this invention vis-a-vis the analogous compounds of the prior art.

The data for the comparison between Compound J and Example 2 is qualified by the fact that the data for Compound J at 6.0 lb/A (6.7 kg/ha) includes effects from three sets of test data as against only one set of test data for the compound of Example 2 at the same rate of application; conversely, the data for the compound of Example 2 at the 1.2 lb/A (1.3 kg/ha) rate was from two sets of data vs. one set of data at the same rate for Compound J. Therefore, in order to further evaluate the relative performances of Compound J and the compound of Example 2, additional comparisons were made in soybeans. It was found that Compound J effected axillary bud development at 0.5 lb/A (0.6 kg/ha) and early pod set and enhanced pod set at application rates of 0.5 lb/A and 1.0 lb/A (1.12 kg/ha); however, these favorable indicators were nullified by an inhibited pod development at both rates of application and leaf distortion at 1.0 lb/A. Moreover, at 2.5 lb/A (2.8 kg/ha) Compound J effected leaf inhibition, leaf distortion, delayed pod set and inhibited pod set. In contrast, the compound of Example 2 exhibited axillary bud development at both 0.5 and 1.0 lb/A, leaf distortion, dark foliar color and delayed pod set at 0.5 lb/A and leaf alteration, delayed pod set, selective apical kill and inhibited pod set at 0.5 lb/A, but no inhibited pod development. Hence, the compound of Example 2 would be superior to Compound J as a plant growth regulator for soybeans.

Additional tests on soybeans with Compound G resulted in plant modifications of axillary bud development and leaf alteration at 0.5 and 1.0 lb/A and inactive pod retention. Additional tests with Compound H resulted in chlorosis and leaf alteration at 0.5 lb/A and axillary bud development and inactive pod retention.

The 4-chloro-2-[N-(4-chlorophenyl)formimidoyl]phenol analog of Compounds G and H caused leaf distortion and delayed and inhibited pod set in soybeans in spite of other favorable plant responses such as dark foliar color and stature reduction.

Similarly as above, comparative data from other tests with Compound I and the compound of Example 1, show that soybeans treated with Compound I at 2.5 lb/A and 1.0 lb/A exhibited leaf distortion and dark foliar color and at 0.5 lb/A exhibited leaf alteration, delayed pod set and stature reduction. However, at each of said rates of application, Compound I resulted in inhibited pod development which is detrimental to soybean yield. In contrast, the compound of Example 1 resulted in leaf alteration, inhibited apical development, early pod set, enhanced pod set and axillary bud inhibition at the higher rate of 5.0 lb/A (5.6 kg/ha).

A more significant and convincing illustration of the unexpected and superior performance of the compounds of this invention vis-a-vis structurally similar compounds representative of the prior art is provided by reference to comparative field test data for the compound of Example 1 and Compound K, i.e., 4-chloro-2-[N-(3,4-dichlorophenyl)formimidoyl]phenol. Compound K appears to be a novel compound, although other analogous 4-halo-2-[N-(mono- and dihalophenyl)-formimidoyl]phenols are known as mentioned above. However, the use of Compound K and its analogs as plant growth regulator compounds was unknown until developed by the inventor herein. By virtue of studies by, and on behalf of the inventor, it was ascertained that Compound K appeared to be the most effective of said prior art compounds as a soybean yield enhancer. Hence, the present comparison is between the preferred compound of this invention and the most effective compound of similar structure of the prior art.

Following the same procedure described in Example 36 above in all particulars, the comparative data obtained for the compound of Example 1 and Compound K is shown in Table 6. In the table, the data in parenthesis in the last four columns expresses the actual quanta for the untreated control plants; the numerical values for the treated plants represent percentages of control plants. "E" and "EP", again, represent the flowering and early pod fill stages, respectively, at which the plant growth regulator solutions were applied as discussed hereinabove.

early pod fill stage. The soybean yield increases are reflected in seeds/ft$^2$ and hundred seed weight values.

It is, therefore, apparent that the compound of Example 1 produces soybean yield increases vis-a-vis those resulting from the use of Compound K that are statistically, economically and patentably significant.

From the foregoing detailed description of the preferred embodiments of the invention, it will be apparent that the new class of compounds disclosed herein have unexpected and superior utility as plant growth regulators. In particular, the compounds of Examples 1, 4 and 6 exhibit markedly unexpected and superior plant growth regulator effects vis-a-vis the closest known compounds of the prior art. In still more particular, the compound of Example 1 has outstanding utility as a soybean pod retention and yield enhancer as shown by reference to field test data set forth in Tables 2–6 above.

In utilizing the method and compositions of this invention, it is often advantageous to treat the crops which are beginning to blossom in order to elicit a growth response to optimize the plants' efficiency in producing fruit.

The methods of this invention can be conveniently carried out in conjunction with agronomic practices such as treating the plants with insecticides, fungicides, nematocides, fertilizer and the like. The application of compositions containing an active ingredient as herein defined and other agricultural chemicals such as selective herbicides, insecticides, fungicides, fertilizers, nematocides and the like are particularly advantageous for obtaining the desired results with minimum treatment costs.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

I claim:

TABLE 6

| Compound | Rate | | | Yield$^a$ | | Population | | Seeds | | Hundred Seed Weight |
|---|---|---|---|---|---|---|---|---|---|---|
|  | Lb/A | (Kg/Ha) | Stage | Bu/A | (Kg/Ha) | × 10$^3$/A | (10$^3$/Ha) | Ft$^2$ | (M$^2$) | (Grams) |
| Ex. 1 | 0 | | | (57) | (3833) | (255) | (630) | (181) | (1946) | (19.8) |
|  | 0.50 | (0.56) | F | 111 | | 95 | | 113 | | 97 |
|  | 1.00 | (1.12) | F | 116 | | 86 | | 119 | | 97 |
|  | 2.00 | (2.24) | F | 112 | | 118 | | 115 | | 96 |
|  | 0.50 | (0.56) | EP | 91 | | 96 | | 96 | | 95 |
|  | 1.00 | (1.12) | EP | 109 | | 116 | | 111 | | 98 |
|  | 2.00 | (2.24) | EP | 116 | | 113 | | 118 | | 97 |
| K | 0 | | | (56.9) | (3827) | (254) | | (181) | | (19.66) |
|  | 0.50 | (0.56) | F | 106 | | 104 | | 113 | | 96 |
|  | 1.00 | (1.12) | F | 103 | | 115 | | 112 | | 92 |
|  | 2.00 | (2.24) | F | 108 | | 114 | | 115 | | 94 |
|  | 0.50 | (0.56) | EP | 80 | | 90 | | 88 | | 91 |
|  | 1.00 | (1.12) | EP | 93 | | 104 | | 104 | | 90 |
|  | 2.00 | (2.24) | EP | 102 | | 119 | | 117 | | 88 |

The data in Table 6 clearly demonstrate the superiority of the compound of Example 1 over Compound K as a soybean yield enhancing agent. It will be noted that the use of the compound of Example 1 resulted in substantially higher yields than Compound K at every rate tested at both stages of application. Particular attention is directed to the comparative soybean yields produced by the compound of Example 1 and Compound K applied at 1.0 and 2.0 lb/A at both the flowering stage and 1. Compounds having the formula

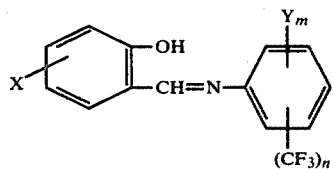

wherein
- X and Y independently represent chlorine, bromine or iodine,
- m is 0–3 and
- n is 1–3.

2. Compounds according to claim 1 wherein X and Y are chlorine, X being in the para position with respect to the hydroxyl radical.

3. Compounds according to claim 1 wherein X is bromine in the para position with respect to the hydroxyl radical.

4. Compounds according to claim 1 wherein m is 0 and n is 1 or 2.

5. Compounds according to claim 1 wherein m is 1 and n is 1 or 2.

6. Compound according to claim 2 which is 4-chloro-2-[N-(2-chloro-5-trifluoromethylphenyl)formimidoyl]phenol.

7. Compound according to claim 2 which is 4-chloro-2-[N-(3-trifluoromethylphenyl)formimidoyl]phenol.

8. Compound according to claim 3 which is 4-bromo-2-[N-(3-trifluoromethylphenyl)formimidoyl]phenol.

9. A plant growth regulating composition consisting essentially of an adjuvant and a non-lethal amount of a compound having the formula

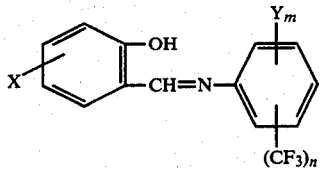

wherein
- X and Y independently represent chlorine, bromine or iodine,
- m is 0–3; and
- n is 1–3.

10. Composition according to claim 9 wherein X and Y are chlorine, X being in the para position with respect to the hydroxyl radical.

11. Composition according to claim 9 wherein X is bromine in the para position with respect to the hydroxyl radical.

12. Composition according to claim 9 wherein m is 0 and n is 1 or 2.

13. Composition according to claim 9 wherein m is 1 and n is 1 or 2.

14. Composition according to claim 10 wherein said compound is 4-chloro-2-[N-(2-chloro-5-trifluoromethylphenyl)formimidoyl]phenol.

15. Composition according to claim 10 wherein said compound is 4-chloro-2-[N-(3-trifluoromethylphenyl)formimidoyl]phenyl.

16. Composition according to claim 11 wherein said compound is 4-bromo-2-[N-(3-trifluoromethylphenyl)formimidoyl]phenol.

17. A method for enhancing pod set and increasing yield of soybean plants which comprises treating said plants with an effective non-lethal amount of a compound having the formula

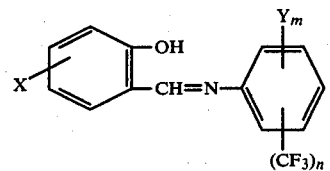

wherein
- X and Y independently represent chlorine, bromine or iodine,
- m is 0–3 and
- n is 1–3.

18. Method according to claim 17 wherein X and Y are chlorine, X being in the para position with respect to the hydroxyl radical.

19. Method according to claim 17 wherein X is bromine in the para position with respect to the hydroxyl radical.

20. Method according to claim 17 wherein m is 0 and n is 1 or 2.

21. Method according to claim 17 wherein m is 1 and n is 1 or 2.

22. Method according to claim 18 wherein said compound is 4-chloro-2-]N-(2-chloro-5-trifluoromethyl)formimidoyl)phenol.